(12) United States Patent
Buforn et al.

(10) Patent No.: US 6,570,021 B2
(45) Date of Patent: May 27, 2003

(54) INTERMEDIATES FOR THE PREPARATION OF 2-IMIDAZOLIN-5-ONES

(75) Inventors: Albert Buforn, Lyons (FR); Alain Gadras, Lyons (FR)

(73) Assignee: Rhone-Poulenc Agro, Lyons (FR)

( * ) Notice: Subject to any disclaimer, the term of this patent is extended or adjusted under 35 U.S.C. 154(b) by 0 days.

(21) Appl. No.: 09/945,675

(22) Filed: Sep. 5, 2001

(65) Prior Publication Data

US 2002/0038034 A1 Mar. 28, 2002

Related U.S. Application Data

(62) Division of application No. 09/230,253, filed as application No. PCT/FR97/01334 on Jul. 17, 1997, now Pat. No. 6,320,057.

(30) Foreign Application Priority Data

Jul. 22, 1996 (FR) .............................................. 96 09483

(51) Int. Cl.[7] ............................................ C07D 277/36
(52) U.S. Cl. ...................................................... 548/183
(58) Field of Search ......................................... 548/183

(56) References Cited

U.S. PATENT DOCUMENTS 6,008,370 A    12/1999  Lacroix et al.
6,320,057 B1 * 11/2001  Bufron .................... 548/318.1

FOREIGN PATENT DOCUMENTS

| AU | 651021 | 7/1993 |
| EP | 0551048 | 7/1993 |
| EP | 0599749 | 6/1994 |
| GB | 2035998 | 6/1980 |
| WO | 93/24467 | 12/1993 |

OTHER PUBLICATIONS

Atkinson et al, *Tetrahedron*, vol. 48, No. 36, pp. 7713–7730 (1992), published by Pergamon Press, Oxford, Great Britain.
Sugi et al, *Bull. Chem. Soc. Japan*, vol. 42, pp. 2984–2989 (1969), published by Chemical Society of Japan, Tokyo, Japan.
Cram et al, *J. Am. Chem. Soc.*, vol. 83, pp. 2183–2189 (1961), published by American Chemical Society, Washington, D.C..
Dahn et al, *Helv. Chim. Acta*, vol. 53, pp. 1370–1378 (1970), published by Verlag Helvetica Chimica Acta, Basel, Switzerland.
Schaumann et al, *Tetrahedron Letters*, No. 16, pp. 1351–1354 (1977), published by Pergamon Press, Oxford, Great Britain. 3/.
Davis et al, *J. Chem. Soc.*, pp. 2419–2425 (1951), published by The Society, London, England.
Hofmann et al, *J. Am. Chem. Soc.*, vol. 74, pp. 470–476 (1952), published by American Chemical Society, Washington, D.C..
Brenner et al, *Helv. Chim. Acta*, vol. XXXVI, pp. 1109–1115 (1953), published by Verlag Helvetica Chimica Acta, Basel, Switzerland.
Garbarino, *Ann. Chimica Ital.*, vol. 59, pp. 841–846 (1969), published by Societa Chimica Italiana, Rome, Italy.

* cited by examiner

*Primary Examiner*—Robert Gerstl
(74) *Attorney, Agent, or Firm*—Burns, Doane, Swecker & Mathis, L.L.P.

(57) ABSTRACT

Novel 2-thiothiazolidin-5-one compounds useful as intermediates for fungicidal 2-imidazolin-5-ones are disclosed.

16 Claims, No Drawings

INTERMEDIATES FOR THE PREPARATION OF 2-IMIDAZOLIN-5-ONES

CROSS-REFERENCE TO RELATED APPLICATIONS

This application is a divisional of U.S. patent application Ser. No. 09/230,253, filed May 6, 1999 now U.S. Pat. No. 6,320,057 now allowed, incorporated by reference herein in its entirety and relied upon, which is the U.S. national stage of International Patent Application No. PCT/FR97/01334, filed Jul. 17, 1997 and designating the United States, and published by the International Bureau in French, not in English, on Jan. 29, 1998 as WO 98/03490.

The present invention relates to novel products which may be used as intermediates for the preparation of 2-imidazolin-5-ones for fungicidal use. The invention also relates to the processes for the preparation of these novel products and to a process which is useful for obtaining these 2-imidazolin-5-ones from these novel intermediates.

2-Imidazolin-5-ones for fungicidal use are known, in particular from European patent publications EP 0551048, EP 0599749 and EP 0629616 and from International publication WO 93/24467.

One aim of the present invention is to propose novel intermediates which allow the preparation of these 2-imidazolin-5-ones.

Another aim of the present invention is to propose a novel route of access to fungicidal 2-imidazolin-5-ones which is of improved safety.

The subject of the invention is thus, firstly, 2-thiothiazolidin-5-ones of general formula (I):

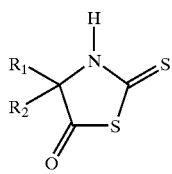

(I)

in which:
 $R_1$ is a $C_1$–$C_3$ alkyl or phenyl radical,
 $R_2$ is an aryl group chosen from phenyl or pyridyl, which is optionally substituted with 1 to 3 groups chosen from a halogen atom, a nitro or cyano group and a $C_1$–$C_3$ alkyl or $C_1$–$C_3$ alkoxy radical; with the exception of 4-ethyl4-phenyl-2-thiothiazolidin-5-one.

The subject of the invention is also the salified forms, as well as the stereoisomers of the compounds of formula (I). The subject of the invention is, in particular, the optical isomers resulting from the presence of an asymmetric carbon, and most particularly, when the radicals $R_1$ and $R_2$ are different, the optical isomers resulting from the presence of the asymmetric carbon bearing $R_1$ and $R_2$. These optical isomers are optically pure compounds or compounds that are highly enriched in one enantiomer. In the following text, the expression optically active compound that is highly enriched in a given enantiomer is understood to refer to a compound containing at least 80%, preferably at least 90%, of this enantiomer. All these compounds are considered as being included in formula (I) defined above.

Among the compounds of formula (I), those are preferred for which:
 $R_1$ represents a $C_1$–$C_3$ alkyl radical,
 $R_2$ represents a phenyl optionally substituted with a halogen atom, a cyano or nitro group or a methyl or methoxy radical.

Even more particularly, among the compounds of formula (I), those for which $R_2$ is a phenyl and $R_1$ is a methyl are preferred.

According to a very advantageous variant of the invention, the compound of formula (I) in which:
 $R_1$ is a methyl and
 $R_2$ is a phenyl, is an enantiomer relative to the asymmetric carbon bearing $R_1$ and $R_2$.

In the present description, all the groups appearing in the chemical formulae which follow, and which have already been defined in the general formula (I), retain the same meaning unless specifically stated otherwise. The alkyl radicals mentioned in the present text may be linear or branched.

One mode of preparation of the compound of formula (I) is now described. This mode of preparation is indicated in the case of compounds which are racemic relative to the carbon bearing the radicals $R_1$ and $R_2$. A person skilled in the art may, however, use these same reactions when he or she wishes to obtain a compound of formula (I) which is enantiomeric relative to the carbon bearing $R_1$ and $R_2$. The reason for this is that the reactions indicated below are entirely stereoselective, in the sense that they do not result in any change in the absolute configuration of this same carbon.

The compound of formula (I) may be obtained by reacting a compound of formula (II) with carbon sulphide, in a solvent or a mixture of solvents, optionally in the presence of a base, at a temperature of between 0° C. and +50° C., according to the following scheme:

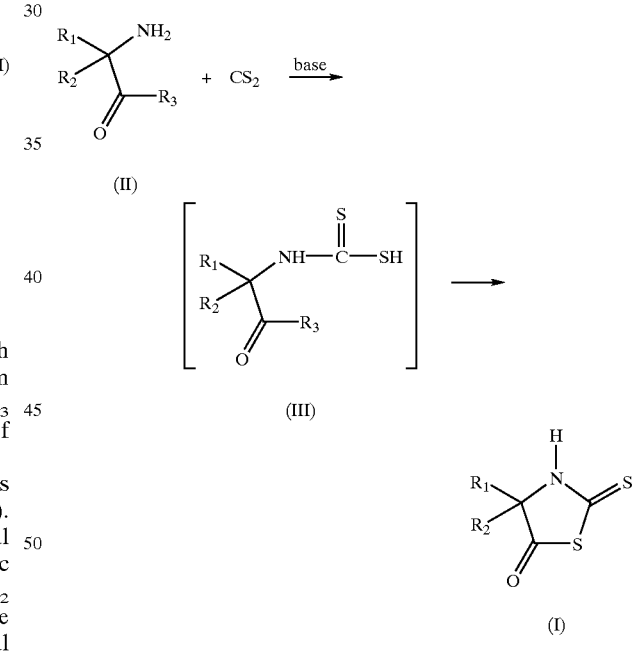

in which $R_3$ is an amino or hydroxyl group or a linear or branched alkoxy radical containing from 1 to 6, preferably from 1 to 3, carbon atoms or a benzyloxy radical optionally substituted with a halogen atom.

The base optionally used may be an inorganic base such as an alkali-metal or alkaline-earth metal hydroxide or carbonate or an organic base such as a primary, secondary or tertiary amine. It may be used in a base/compound II ratio (expressed as number of moles) of between 0.05 and 1.2, preferably between 0.1 and 1.

In this scheme, the compound of formula (III) may be isolated as an intermediate, in the case where a base is used, in the form of a salt.

Solvents which may be used are water, ethers, cyclic ethers, alkyl esters, dipolar solvents such as acetonitrile, alcohols of 1 to 4 carbon atoms, aromatic solvents, preferably toluene, dichloromethane or chloroform, and carbon sulphide. Mixtures of solvents which may be used are the mixture of one or more alcohols with one or more of the abovementioned solvents.

When $R^3$ is a hydroxyl group, it is preferred to use water as solvent.

When $R^3$ is other than a hydroxyl group, it is preferred to use an alcohol/water mixture as solvent.

In the case where the compound of formula (III) is isolated, it may be converted directly into compound (I) by heating to a temperature ranging from 25° C. to the reflux temperature of the solvent used. The conversion of intermediate compound (III) into compound (I) may also be carried out by treatment with a strong acid which is either an inorganic acid such as hydrochloric acid or sulphuric acid, or an organic acid such as trifluoroacetic acid.

It is preferred to carry out this process in the absence of base or at a temperature of between 20 and 40° C. In this case, the compound of formula (III) is not isolated.

Other modes of the procedure which allow compound (I) to be prepared starting from (II) are described by A. C. Davis and A. J. Levy in *J. Chem Soc.*, pp. 2419–25 (1951) or by K. Hofmann et al. in *J. Am. Chem. Soc.*, vol. 74, pp. 470–476 (1952).

The α-amino ester of formula (II) in which $R_3$ is an alkoxy radical may be obtained by esterification of the corresponding α-amino acids according to a procedure similar to that described by M. Brenner and W. Huber in *Helv Ch. Acta.* (1953), volume 36, pages 1109–1115.

The α-amino amide of formula (II) in which $R_3$ is an amino group may be obtained from an amino ester by the action of ammonia as described by J. A. Garbarino in *Ann. Chimica Ital.* vol. 59, pp. 842–849 (1969).

The α-amino acids are prepared by reactions and methods that are known per se.

When the compound of formula (II) is an amino ester enantiomer, it may be obtained in particular by:

diastereoselective amination of a prochiral compound followed by deprotection of the chiral couple as described by R. S. Atkinson et al, *Tetrahedron*, 1992, 48, pp. 7713–30, or by resolution of the corresponding racemic mixture with a chiral compound, as described by Y. Sugi and S. Mitsui, *Bull. Chem. Soc. Japan*, 1969, 42, pp. 2984–89, or alternatively by esterification of a chiral amino acid, as described by D. J. Cram et al., *J. Am. Chem. Soc.*, 1961, 83, pp. 2183–89.

When the compound of formula (II) is an amino amide enantiomer, it may be obtained either starting from a chiral amino ester or by resolution of the corresponding racemic mixture, as described by H. Dahn et al. in *Helv. Chim. Acta*, vol. 53, pp. 1370–1378 (1970).

The 2-thiothiazolidin-5-ones of formula (I) are useful for the preparation of fungicidal 2-imidazolin-5-ones of formula (IV):

(IV)

in which:

M represents an oxygen or sulphur atom;

$R_{30}$ represents a linear or branched alkyl radical containing from 1 to 6 carbon atoms or a linear or branched haloalkyl radical containing from 1 to 6 carbon atoms;

$R_4$ represents a hydrogen atom or an acyl radical;

$R_5$ represents an aryl or heteroaryl radical chosen from: phenyl, naphthyl, pyridyl, pyrimidinyl, pyridazinyl, pyrazinyl, thienyl, benzothienyl, furyl, benzofuryl, quinolyl, isoquinolyl or methylenedioxyphenyl, each of these radicals optionally being substituted with 1 to 7 groups, which may be identical or different, preferably from 1 to 3, chosen from the meanings of $R_{51}$ defined below;

$R_{51}$ represents:
  a halogen atom or
  an alkyl, haloalkyl, alkoxy, haloalkoxy, alkylthio, haloalkylthio or alkylsulphonyl radical, which is linear or branched, of 1 to 6 carbon atoms, or
  a cycloalkyl, halocycloalkyl, alkenyloxy, alkynyloxy, alkenylthio or alkynylthio radical of 3 to 6 carbon atoms, or
  a nitro or cyano group, or
  an amino radical optionally mono- or disubstituted with an alkyl or acyl radical of 1 to 6 carbon atoms or alkoxycarbonyl radical of 2 to 6 carbon atoms;

as well as the agriculturally acceptable salified forms of these compounds and their stereoisomers, in particular, when $R_1$ and $R_2$ are different, the optical isomers resulting from the presence of the asymmetric carbon bearing the radicals $R_1$ and $R_2$.

The preparation of the fungicidal compounds of formula (IV) starting from the 2-thiothiazolidin-5-ones of formula (1) which form the subject of the invention is now described, according to a process which may be used either in a racemic series or in an enantiomeric series.

The compound of formula (I) is reacted with a compound of formula (V) in a solvent and at a temperature of between +20° C. and +100° C., preferably between 40 and 80° C., according to the following scheme:

(I)    (V)

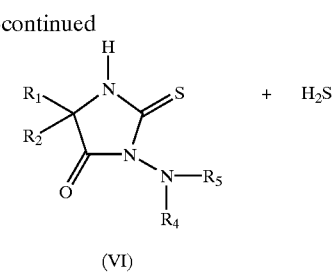

(VI)

Solvents which may be used are, for example, dioxane, a dipolar aprotic solvent, in particular N-methylpyrrolidone, dimethylformamide, dimethyl sulphoxide or acetonitrile, an alcohol comprising from 1 to 4 carbon atoms and more particularly methanol, an aromatic solvent and more specifically pyridine or monochlorobenzene.

It is preferred to carry out this reaction using a catalyst chosen from a tertiary amine such as triethylamine or tributylamine, or an organic salt of this amine, such as tributylamine acetate. This catalyst is present in a catalyst/compound (I) proportion (expressed as number of moles) ranging from 0.05 to 1, preferably from 0.1 to 0.5. In this case, improved purity is obtained.

The thiohydantoin of formula (VI) is converted into 2-imidazolin-5-one of formula (IV) according to a process described in one of the patent publications EP 0551048, EP 0599749 and EP 0629616.

The examples which follow are given purely by way of illustration of the compounds and preparation processes which form the subject of the invention. They do not in any way limit this invention. The structure of the derivative illustrated was established using at least one of the following spectral techniques: proton NMR spectrometry, carbon 13 NMR spectrometry, infrared spectrometry and mass spectrometry, as well as the usual methods for measuring optical rotations.

EXAMPLE No. 1

Preparation of (4S)-4-methyl-4-phenyl-2-thiothiazolidin-5-one from an amino amide 3.26 g (20 mmol) of (2S)-2-amino-2-phenylpropionamide, 6 ml (100 mmol) of carbon sulphide and 4 ml of acetonitrile are introduced into a 50 ml round-bottomed flask fitted with a mechanical stirrer. The heterogeneous medium is kept stirring for 20 h at 20° C. After distillation under vacuum of the excess carbon sulphide and the acetonitrile, and after purification and filtration, 3.70 g of (4S)-4-methyl-4-phenyl-2-thiothiazolidin-5-one are obtained in the form of a white solid melting at 104° C., corresponding to a yield of 83%.

EXAMPLE No. 2

Preparation of (4S)-4-methyl-4-phenyl-2-thiothiazolidin-5-one from an amino ester 2 g (11.1 mmol) of methyl (2S)-2-amino-2-phenylpropionate, 15 ml of tetrahydrofuran, 1.82 ml (13 mmol) of triethylamine and 0.78 ml (13 mmol) of carbon sulphide are introduced into a 25 ml test tube fitted with a magnetic stirrer. After hermetic closure, the test tube is maintained at 45° C. and the homogeneous medium is kept stirring for 4 h at this temperature.

After cooling and purification, 2 g of (4S)-4-methyl-4-phenyl-2-thiothiazolidin-5-one are obtained in the form of a white powder, i.e. a yield of 80%.

EXAMPLE No. 3

Preparation of (4S)-4-methyl-4-phenyl-1-phenylamino-2-thiohydantoin 893 mg (4 mmol) of (4S)-4-methyl-4-phenyl-2-thiothiazolidin-5-one, 8 ml of acetonitrile and 100 µl (0.4 mmol) of tributylamine are introduced into a 25 ml round-bottomed flask fitted with a magnetic stirrer. The mixture is heated to 70° C. and a solution of 520 mg (4.8 mmol) of phenylhydrazine in 4.5 ml of acetonitrile is then run in over 2 h. The reaction medium is heated at 80° C. for 6 h. After cooling, the acetonitrile is removed by distillation under reduced pressure. After purification, 975 mg of (4S)-4-methyl-4-phenyl-1-phenylamino-2-thiohydantoin are obtained in the form of a white solid melting at 167° C., the purity of which, measured by HPLC, is 100%, i.e. a yield of 82%.

EXAMPLE No. 4

Preparation of (4S)-4-methyl-4-phenyl-2-thiothiazolidin-5-one from (2S)-2-amino-2-phenylpropionic acid 11 g ($10^{-2}$ mol) of (2S)-2-amino-2-phenylpropionic acid (in the form of a mixture containing 15% by weight of amino acid in solid NaCl), 10 ml of N-methylpyrrolidone, 0.8 g ($2\times10^{-2}$ mol) of NaOH pellets and then 1.8 ml ($3\times10^{-2}$ mol) of carbon disulphide are successively introduced into a 50 ml round-bottomed flask fitted with a magnetic stirrer. After hermetic closure, the reaction medium is heated at 60° C. for 5 hours with vigorous stirring. After cooling, 50 ml of water and then 5.4 ml of concentrated $H_2SO_4$ are added to the reaction medium. The organic phase is extracted, washed, dried and then concentrated. (4S)-4-Methyl-4-phenyl-2-thiothiazolidin-5-one is obtained in a yield of 84%.

What is claimed is:

1. A 2-thiothiazolidin-5-one compound having the formula (I):

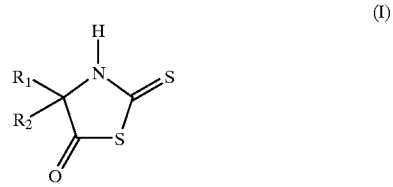

wherein:
$R_1$ is a $C_1$–$C_3$ alkyl or phenyl radical; and
$R_2$ is a phenyl or pyridyl radical, said radical being optionally substituted with 1 to 3 substituents selected from the group consisting of a halogen atom, a nitro or cyano group and a $C_1$–$C_3$ alkyl or $C_1$–$C_3$ alkoxy radical;
with the exception of 4-ethyl-4-phenyl-2-thiothiazolidin-5-one;
provided that $R_1$ and $R_2$ are different and the compound is an enantiomer relative to the asymmetric carbon atom bearing $R_1$ and $R_2$;
said compound being optically pure or highly enriched in said enantiomer.

2. A compound according to claim 1, wherein:
$R_1$ is a $C_1$–$C_3$ alkyl radical; and
$R_2$ is a phenyl radical optionally substituted with a halogen atom, a cyano or nitro group or a methyl or methoxy radical.

3. A 2-thiothiazolidin-5-one compound having the formula (I):

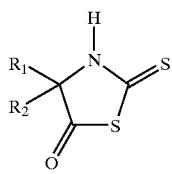
(I)

wherein:

$R_1$ is a methyl radical;

$R_2$ is a phenyl radical;

and the compound is an enantiomer relative to the asymmetric carbon atom bearing $R_1$ and $R_2$;

said compound being optically pure or highly enriched in said enantiomer.

4. The compound which is (4S)-4-methyl-4-phenyl-2-thiothiazolidin-5-one, said compound being optically pure or highly enriched in (4S) enantiomer.

5. A process for the preparation of a compound having the formula (I):

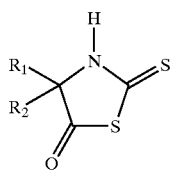
(I)

wherein:

$R_1$ is a $C_1$–$C_3$ alkyl or phenyl radical;

$R_2$ is a phenyl or pyridyl radical, said radical being optionally substituted with 1 to 3 substituents selected from the group consisting of a halogen atom, a nitro or cyano group and a $C_1$–$C_3$ alkyl or $C_1$–$C_3$ alkoxy radical;

or a salified form or stereoisomer thereof;

with the exception of 4-ethyl-4-phenyl-2-thiothiazolidin-5-one;

said process comprising reacting a compound having the formula (II) below with carbon sulphide, in a solvent or a mixture of solvents, optionally in the presence of a base, at a temperature of between 0° C. and 50° C., according to the scheme:

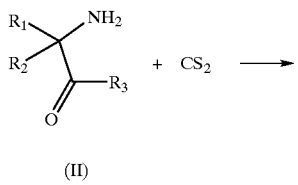
(II)

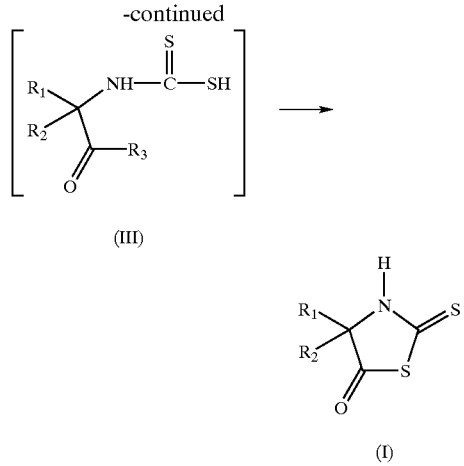
(III)
(I)

wherein $R_1$ and $R_2$ are as defined above and $R_3$ is an amino or hydroxyl group, a linear or branched alkoxy radical having from 1 to 6 carbon atoms or a benzyloxy radical optionally substituted with a halogen atom.

6. A process according to claim 5, wherein $R_3$ is an amino or hydroxyl group, a linear or branched alkoxy radical having from 1 to 3 carbon atoms or a benzyloxy radical optionally substituted with a halogen atom.

7. A process according to claim 5, carried out in the absence of base or at a temperature of between 20° C. and 40° C.

8. A process according to claim 5, wherein:

$R_1$ is a $C_1$–$C_3$ alkyl radical; and $R_2$ is a phenyl radical optionally substituted with a halogen atom, a nitro or cyano group or a methyl or methoxy radical.

9. A process for the preparation of a 2-thiothiazolidin-5-one compound having the formula (I):

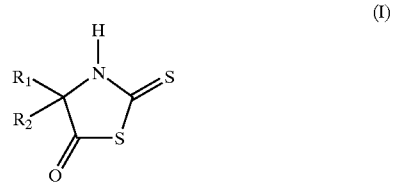
(I)

wherein:

$R_1$ is a $C_1$–$C_3$ alkyl or phenyl radical; and $R_2$ is a phenyl or pyridyl radical, said radical being optionally substituted with 1 to 3 substituents selected from the group consisting of a halogen atom, a nitro or cyano group and a $C_1$–$C_3$ alkyl or $C_1$–$C_3$ alkoxy radical;

with the exception of 4-ethyl-4-phenyl-2-thiothiazolidin-5-one;

provided that $R_1$ and $R_2$ are different and the compound is an enantiomer relative to the asymmetric carbon atom bearing $R_1$ and $R_2$;

said process comprising reacting a compound having the formula (II) below with carbon sulphide, in a solvent or a mixture of solvents, optionally in the presence of a base, at a temperature of between 0° C. and 50° C., according to the scheme:

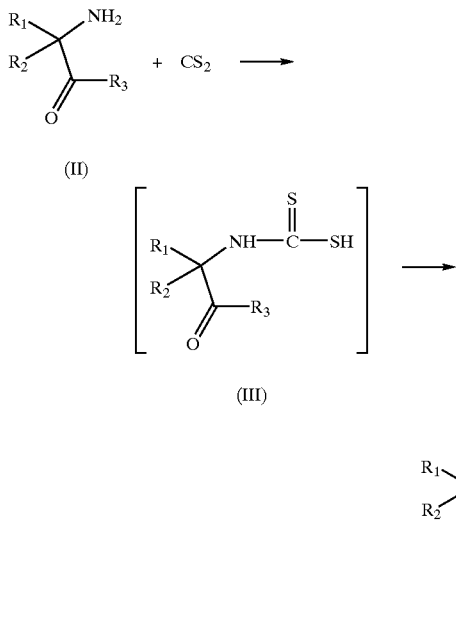

(II)

(III)

(I)

wherein $R_1$ and $R_2$ are as defined above and $R_3$ is an amino or hydroxyl group, a linear or branched alkoxy radical having from 1 to 6 carbon atoms or a benzyloxy radical optionally substituted with a halogen atom.

10. A process according to claim 9, wherein:

$R_1$ is a $C_1$–$C_3$ alkyl radical; and $R_2$ is a phenyl radical optionally substituted with a halogen atom, a cyano or nitro group or a methyl or methoxy radical.

11. A process for the preparation of a 2-thiothiazolidin-5-one compound having the formula (I):

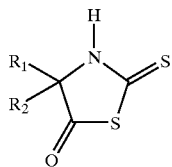

(I)

wherein:

$R_1$ is a methyl radical; and $R_2$ is a phenyl radical;

or a salified form or stereoisomer thereof;

said process comprising reacting a compound having the formula (II) below with carbon sulphide, in a solvent or a mixture of solvents, optionally in the presence of a base, at a temperature of between 0° C. and 50° C., according to the scheme:

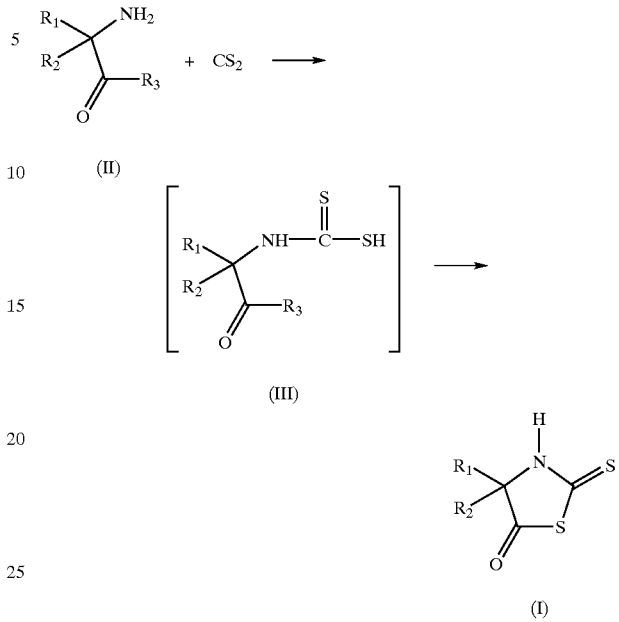

(II)

(III)

(I)

wherein $R_1$ and $R_2$ are as defined above and $R_3$ is an amino or hydroxyl group, a linear or branched alkoxy radical having from 1 to 6 carbon atoms or a benzyloxy radical optionally substituted with a halogen atom.

12. A process for the preparation of a 2-thiothiazolidin-5-one compound having the formula (I):

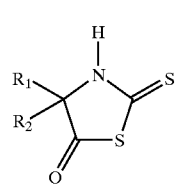

(I)

wherein:

$R_1$ is a methyl radical;

$R_2$ is a phenyl radical;

and the compound is an enantiomer relative to the asymmetric carbon atom bearing $R_1$ and $R_2$;

said process comprising reacting a compound having the formula (II) below with carbon sulphide, in a solvent or a mixture of solvents, optionally in the presence of a base, at a temperature of between 0° C. and 50° C., according to the scheme:

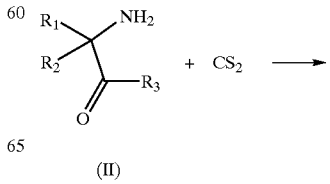

(II)

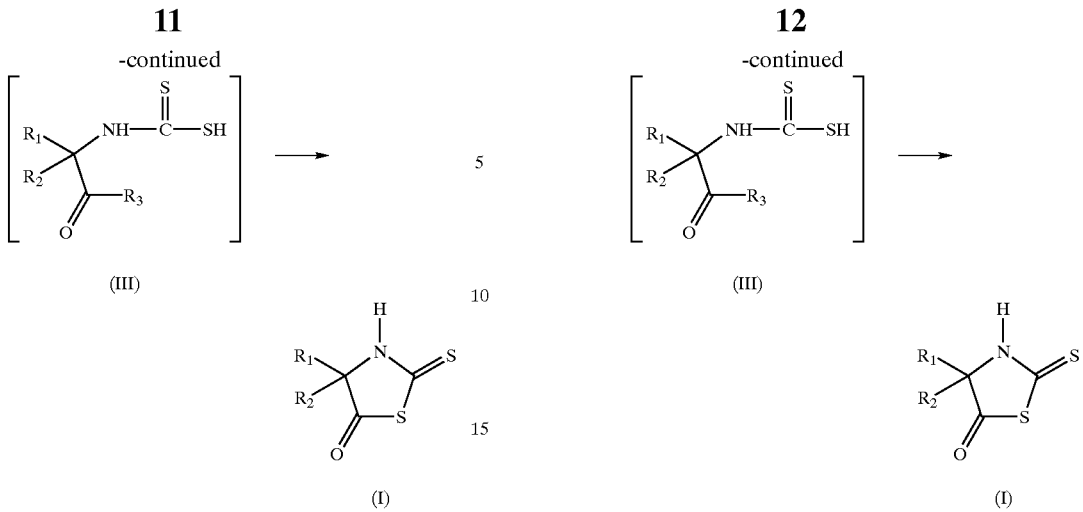

wherein $R_1$ and $R_2$ are as defined above and $R_3$ is an amino or hydroxyl group, a linear or branched alkoxy radical having from 1 to 6 carbon atoms or a benzyloxy radical optionally substituted with a halogen atom.

13. A process for the preparation of (4S)-4-methyl4-phenyl-2-thiothiazolidin-5-one, said process comprising reacting a compound having the formula (II) below with carbon sulphide, in a solvent or a mixture of solvents, optionally in the presence of a base, at a temperature of between 0° C. and 50° C., according to the scheme:

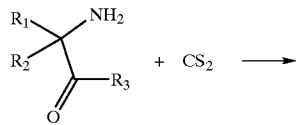

(II)

wherein $R_1$ is a methyl radical, $R_2$ is a phenyl radical and the compound of formula (II) is the (2S)-enantiomer, and $R_3$ is an amino or hydroxyl group, a linear or branched alkoxy radical having from 1 to 6 carbon atoms or a benzyloxy radical optionally substituted with a halogen atom.

14. A process according to claim 13, comprising reacting (2S)-2-amino-2-phenylpropionamide with carbon sulphide.

15. A process according to claim 13, comprising reacting (2S)-2-amino-2-phenylpropionate with carbon sulphide.

16. A process according to claim 13, comprising reacting (2S)-2-amino-2-phenylpropionic acid with carbon disulphide.

* * * * *